(12) United States Patent
Knowles

(10) Patent No.: US 6,420,352 B1
(45) Date of Patent: Jul. 16, 2002

(54) HAIR LOSS PREVENTION

(76) Inventor: W. Roy Knowles, 7500 San Felipe, Suite 850, Houston, TX (US) 77003

( * ) Notice: Subject to any disclaimer, the term of this patent is extended or adjusted under 35 U.S.C. 154(b) by 0 days.

(21) Appl. No.: 10/044,553

(22) Filed: Jan. 11, 2002

Related U.S. Application Data

(63) Continuation of application No. 09/619,142, filed on Jul. 19, 2000.

(51) Int. Cl.[7] ........................ A61K 31/56; A61K 31/496
(52) U.S. Cl. ............. 514/171; 514/255.05; 514/255.06; 514/947
(58) Field of Search ............................ 514/171, 255.05, 514/255.06

(56) References Cited

U.S. PATENT DOCUMENTS

| | | | | |
|---|---|---|---|---|
| 4,863,970 A | * | 9/1989 | Patel et al. | |
| 4,946,870 A | * | 8/1990 | Partain, III et al. | |
| 5,053,403 A | * | 10/1991 | Orentreich et al. | |
| 5,183,817 A | * | 2/1993 | Bazzano | |
| 5,482,965 A | * | 1/1996 | Rajadhyaksha | |
| 5,574,011 A | * | 11/1996 | Tien | |
| 5,652,256 A | * | 7/1997 | Knowles | |
| 5,723,149 A | * | 3/1998 | Bonte et al. | |
| 5,994,319 A | * | 11/1999 | Hoke, Jr. | |
| 6,124,362 A | * | 9/2000 | Bradbury et al. | |
| 6,162,801 A | * | 12/2000 | Kita | |

OTHER PUBLICATIONS

Kincl et al., Increasing oral bio availability of progesterone by formulation, abstract, J. Steroid Biochem., 1978, vol. 9(1), pp. 83–84.*

* cited by examiner

*Primary Examiner*—Theodore J. Criares
*Assistant Examiner*—Vickie Kim
(74) *Attorney, Agent, or Firm*—Pharmaceutical Patent Law, LLC; Mark Pohl, Esq.

(57) ABSTRACT

Compositions to prevent or reduce hair loss, allowing the body to maintain normal, healthy hair growth, comprising a penetration enhancer together with a testosterone blocker or a vascular enhancer, or both.

17 Claims, No Drawings

HAIR LOSS PREVENTION

This application is a continuation of Ser. No. 09/619,142 filed Jul. 19, 2000.

BACKGROUND

My invention relates to preparations useful for maintaining normal, healthy hair bulb function, for preventing hair loss, and for medically treating androgenic alopecia and like dermatological diseases. I will first review pertinent hair biology, then discuss prior art teachings in the field, and then describe my invention.

Hair Biology

Hair bulbs are responsible for normal, healthy hair growth and retention. Hair bulbs are located in the skin, about 3/16 of an inch below the skin surface. They are located just above the fatty layer at the very lower most position of the skin.

The majority of facial and body hair growth is stimulated by androgens. However, the growth of scalp hair has been shown, in genetically programmed individuals, to be inhibited by 5α-dihydrotestosterone ("DHT") in individuals who exhibit a hereditary pre-disposition to baldness. Ebling, *Dermatol. Clin. S.* 467 (1987); Lucky, 4 *Biochem. Soc. Transc.* 597 (1988); Brodland et al., 47 *Cutis* 173 (1991). DHT is produced by reducing testosterone with a 5α-reductase enzyme. The phenotypic expression of baldness does not occur in the absence of testosterone. Androgenic alopecia or common baldness represents 99 percent of all cases of hair loss. Broadland, id.

The mechanism through which androgens regulate the biology of hair is by modulating the hair growth cycle. Ebling, 4 *Biochem. Soc. Trans.* 597; Bergfield et al., 5 *Dermatol. Clin.* 491. The effect of DHT on hair growth appears to be related to local rather than systemic levels of the hormone. This is because the capacity of scalp skin from balding individuals to convert testosterone ("T") to DHT is greater than that observed in the scalp of non-balding individuals. Lucky, supra; Schweikert et al., 38 *J. Clin. Endocrinol. Metab.* 811.

To prevent hair loss, maintain the health of hair bulbs, or to treat baldness, several compositions are known in the art. We discuss them now.

Hair Loss Prevention

Hair loss prevention preparations are known in the art. These include natural product preparations, biological products, vascular toners and testosterone blockers. Several prior art compositions are discussed in the accompanying Petition To Make Special and its accompanying references, the contents of which are incorporated herein by reference.

Natural Products. Several inventors disclose natural compositions. Casero, U.S. Pat. No. 5,340,579, discloses a composition comprising (a) mucopolysaccharides, (b) human umbilical cord extract, (c) tetrahydrofurfuryl nicotinate, and (d) pharmaceutically and cosmetically acceptable excipients. Buck, U.S. Pat. No. 5,512,275 and 5,609,858, discloses a formulation for the treatment of androgenic alopecia, comprising liquor carbonis detergens in combination with spirits of camphor, castor oil, isopropyl alcohol. Chizick et al., U.S. Pat. No. 5,972,345, discloses a combination of saw palmetto extract, African pygeum extract, and stinging nettle extract.

Biological Products. Hoke, U.S. Pat. No. 5,994,319, discloses using genetic material as a anti alopecia therapeutic. Hoke proposes using anti-sense oligonucleotides targeting 5-α reductases in conjunction with other hair growth enhancers. Tien, U.S. Pat. No. 5,574,011, discloses the use of a class of LHRH analogs for treating male pattern baldness. Messenger, U.S. Pat. No. 6,020,327, discloses administering aromatase inhibitors to treat hair loss. Liao et al., U.S. Pat. Nos. 5,422,371 and 5,605,929, discloses a class of anti-androgenic compounds.

Vascular Toners. Several organic chemicals are known to affect the hair growth and hair retention cycle. These include minoxidil. I refer to minoxidil and similar kinds of compounds as "vascular toners," because they are believed to be effective due to their impact on local blood circulation.

Minoxidil has been shown to stimulate hair growth or inhibit the loss of hair in a number of patients beginning to develop androgenic alopecia. Minoxidil is the generic name for 6-(1-piperidinyl)-2, 4-pyrimidinediamaine 3-oxide. Its preparation is disclosed in Anthony, W. C. et al., U.S. Pat. No. 3,382,247 (1968); McCall, J. M., et al., 40 *J. Organic Chem.* 3304 (1975); Gorecki, D. K. J., 17 *Analytical Profiles of Drug Substances* 185 (Academic Press, New York 1988). It is more soluble (by weight minoxidil/volume of solvent) in non-polar solvents than polar ones (75 mg/ml in propylene glycol; 44 mg/ml in methanol; 6.5 in dimethyl sulfoxide; 2.2 mg/ml water).

Minoxidil is medically classified as an anti-hypertensive. It affects heart rate and rhythm. It has thus been used in an oral formulation as a cardiac drug. Andersson, O., 205 *Acta Med. Scand.* 213 (1979); Moser, M., 26 *Advan. Cardiol.* 38 (1979). over dosage may create cardiac arrhythmias or other adverse side effects. See e.g., Carlson, E. S., 39 *Toxicol. Applied Pharmacol.* 1 (1977).

Minoxidil is also medically classified as an anti-alopecia agent. Its efficacy in treating early male pattern baldness has been described in numerous published articles. E.g., Olsen, E. A. et al., 13 *J. Am. Acad. Dermatol.* 185 (1985); Novak, E., 24 *Int. J. Dermatol.* 82 (1982). Its limited percutaneous absorption and secretion is described in Franz, J. T., 121 *Arch. Dermatol.* 203 (1985).

The mechanism by which minoxidil alters the hair growth cycle is uncertain. It is thought to act by increasing vascular circulation to the hair follicle. It is known that minoxidil effectiveness is more pronounced in scalp areas which are more vascular.

Topical minoxidil is know to have certain shortcomings. It is effective in only about eight percent of adult male users. It produces "lanugo," or baby-type, hair which is relatively thin. Further, and perhaps most significantly, after approximately 30 months of continuous use, minoxidil shows a sharp drop in effectiveness. After about thirty months of use, about half of the new hair growth falls out. Thus, while the user has somewhat more hair than originally, the user has less hair than originally seen.

Testosterone Inhibitors. Inhibitors of steroid metabolism, particularly those that inhibit the conversion of testosterone to dihydro testosterone, have shown effects on hair cycles, including inhibition of hair loss. One class of enzymes targeted by these inhibitors are the steroid 5-α reductases.

Certain 5α-reductase inhibitors have been shown to inhibit hair loss. For example, stump-tail macaque monkeys treated with the 5α-reductase inhibitor 17b-N,N,-dimethylcarbamoyl- 4-methyl- 4-aza-5α-androstan- 3-one undergo significantly less age related hair loss than untreated monkeys. Rittmaster et al., 65 *J. Clin. Endocrinol. Metab.* 188 (1987). Similarly, finasteride, a 5α-reductase inhibitor, miniaturizes scalp hair follicles, reversing the balding process. "Merck's Propecia Shows Promise In Hair Loss," *Marketletter* (Mar. 31, 1997). These inhibitors are thought to work by inhibiting the reduction of testosterone to DHT, as DHT is considered to be the more active form. The use of a combination of finasteride and minoxidil demonstrated that, in combination, these two drugs increased the rate of hair growth when compared to either compound administered alone. Diani, 74 *J. Clin. Endocrinol. Metabol.* 345.

Minoxidil used in conjunction with effectors of steroid metabolism, leads to enhanced hair growth and decreased rates of hair loss.

Testosterone blockers are known in the art (I use the term "testosterone blocker" to denote a competitive antiandrogen which inhibits the binding of testosterone or DHT onto its cell surface binding site, rather than a compound which is used to inhibit the reduction of testosterone into DHT.). Also known is their use systemically (orally or intravenously). As systemic therapeutics, they are known in the art as having a key shortfall: their long term efficacy is compromised by their blocking of the androgenic feedback inhibition of gonadotropin secretion. This interference results in elevated gonadotropin secretion, which in turn increases testicular secretion of testosterone. The higher level of testosterone eventually overcomes the action of the antiandrogen. Liao, supra, at col. 3, lines 16–31.

Thus, what is needed in the art is a safe and effective way to maintain both the healthy function of hair bulbs, and the health of existing hair, that avoids the shortfalls seen in the prior art.

SUMMARY

I have invented a kind of hair loss prevention composition. My invention is a new combination of already known types of compounds. My invention can be used either cosmetically (to maintain healthy hair growth) or pharmaceutically (to treat a medical condition). It can be made using components already known in the art, allowing one to enjoy the predictability of use available with these old compounds. My invention is flexible enough, however, to also allow one to substitute newly-discovered compounds substantially equivalent to the already known compounds. Thus, my invention can be adapted to allow the user to use the safest, most effective components then available.

I have found that certain compounds have greatly improved effectiveness - achieving ten times the benefit, or an entire order of magnitude - if combined with a skin penetration enhancer. The penetration enhancer delivers these compounds to the hair bulb, where the compounds are most needed.

I have thus found that testosterone blockers, if applied topically (rather than systemically administered), are effective in preventing hair loss, and if used in conjunction with a dermal penetration enhancer. Such topical use avoids precipitating the systemic increase in testosterone production seen with oral administration, by minimizing systemic interference with normal gonadotropin secretion. I have also found that vascular toners, if applied topically in conjunction with a dermal penetration enhancer, work much better.

DETAILED DESCRIPTION

My invention includes a skin penetration enhancer used together with a testosterone blocker or a vascular enhancer, or both. I first discuss each component individually, and then discuss the combinations of these components that I have found most acceptable.

Penetration Enhancers

You can use a variety of skin penetration enhancers to make compositions that work as I intend. Penetration enhancers and skin penetrating formulations are known in the art. These include the variety of formulations used from time to time for both psoriasis treatment pharmaceuticals, and psoriasis prevention nutritional supplements and cosmetics.

The penetration enhancer (or penetration agent) should be accepted for human use by relevant government agencies. Thus, dimethyl sulfoxide, while within the scope of the claims, is not a preferred penetration enhancer where that compound is not approved for human topical use. The penetration enhancer should not chemically react with any other ingredient to impair or alter the composition's stability and shelf life. Thus, one should examine the possible reactivity of a given penetration enhancer with a given testosterone blocker or vascular toner.

The penetration agent should be cosmetically acceptable. Thus, while I have tested dimethyl acetate, I do not favor it. While it is within the scope of the claims, it is a weak penetration enhancer. Thus, one needs to use a lot of it. In these high amounts, it smells bad. In contrast, methyl acetate is odorless, and I have tested and found it acceptable.

Several inventors disclose liposome technology to deliver cosmetic and dermatology materials. See, for example, Lishko et al., U.S. Pat. No. 5,753,263, discloses using liposomes to selectively deliver a composition to hair follicles. Liposomes are made of fatty material, and are suitable for delivering homogenous types of materials. As such, it may be difficult for a liposome to in fact work with a combination of a polar compound (like a minoxidil vascular toner) and a non-polar compound (such as a progesterone testosterone blocker). I thus do not consider liposome technology within the scope of the term "penetration enhancer" in this patent.

Vascular Toners

My invention works with a variety of vascular toners. One can make compositions within the scope of my invention with minoxidil analogs or derivatives, or with other anti-alopecia agents, such as diphencyprone, which work in a similar way, by improving local blood flow to the affected hair bulbs. Because it has such a broad volume of use and scientific study, I prefer to use minoxidil. I thus use it as an example throughout this specification.

A vascular toner, if used to maintain healthy function of hair bulbs, must be delivered to the small blood vessels feeding the hair bulbs. I have thus found that the effectiveness of the vascular toner is greatly improved if it is topically applied along with a penetration enhancer. This allows the vascular toner to act locally.

The vascular toner must be carefully titrated against the penetration enhancer. For example, for a given concentration of minoxidil, one needs to use the penetration enhancer in the appropriate concentration. If a given penetration enhancer is used in a too high concentration, the minoxidil may penetrate through the skin and reach the systemic blood circulation. It can there, if present in sufficient amount, cause side effects as seen by taking oral minoxidil. Thus, it is necessary to adjust the amounts of penetration enhancer and vascular toner, depending on the concentration and specific identity of the enhancer and the toner.

Adding a penetration enhancer to the vascular toner appears to fundamentally change the biological mechanism by which the vascular toner works. This is shown by the qualitatively different results seen between minoxidil and my compounds. The two products produce different types of hair, and for different time periods.

Minoxidil without a penetration enhancer (as available in ROGAINE™ topical minoxidil U.S.P.) produces a different kind of hair than does minoxidil used with a penetration enhancer. It is known in the art that topical minoxidil without a penetration enhancer (as is commercially available in ROGAINE (™) topical minoxidil U.S.P., commercially available from Pharmacia & Upjohn Inc., Bridgewater, N.J.) results in thin, baby-like, temporary hair, called "lanugo" hair. I have found that my compounds, by contrast, result in good, coarse, "terminal" hair, hair which is normal, permanent adult hair.

This indicates that minoxidil without and with penetration enhancer may act on different types of hair bulbs, or produce different responses from the same hair bulbs. Minoxidil without enhancer is only weakly soluble in polar solvents. See supra. It thus has difficulty diffusing to the deeply located hair bulbs (roots) which are located just above the deep fat layer. Minoxidil without enhancer may thus affect only hair bulbs located close to the skin surface, or located in a less fatty skin layer, or hair bulbs most sensitive to changes in blood flow. Alternatively, it may affect the same hair bulbs, but with such weak or attenuated effect that the hair bulbs produce a different type of hair.

In contrast, my compounds produce normal, terminal hair. This indicates that my compounds act directly on the mature, adult hair bulbs responsible for terminal hair growth.

Further, it is known in the art that minoxidil users experience a sudden drop in hair thickness after about thirty months of usage. I thus have sought the time at which my compounds have a sudden drop in effectiveness. Surprisingly, I have found that my compounds apparently do not lose effectiveness at all, even after using them for substantially greater than thirty months. This confirms that while my compounds appear to simply restore or preserve normal hair bulb function, the prior art compositions do not restore normal hair bulb function, but actually provoke an abnormal function—the growth by an adult of baby like, temporary hair. That this function is abnormal is confirmed by its drop in effectiveness after thirty months; such a drop in efficacy indicates a "tolerance" acquired against the intervention, rather than the maintenance of a permanent, healthy state.

This indicates that the physiological mechanisms and biomedical pathways of the two preparations are different. Minoxidil alone, in the concentrations typically used, may actually temporarily alter a normal adult body function (causing the adult body to temporarily produce infant hair). In contrast, my invention simply maintains the normal function of the healthy adult body hair bulb, allowing it to continue to produce normal adult hair as long as the compound is used.

I have also found that the effect of the formulations depends on location of administration. Using the specific formulations disclosed here, I have observed decreases in hair loss, and a consequent statistically significant increase in the amount of healthy mature hair, after 4.0–4.5 months on the frontal scalp. On the crown and back of the head, by contrast, I have observed statistically significant results after 4.5–5.0 months. The frontal scalp may react faster because it enjoys greater vascularization and blood flow than the other parts of the scalp.

Testosterone Blocker

My invention works with a variety of testosterone blockers. I prefer to use a blocker already approved for human use by the United States Food & Drug Administration, as these types of testosterone blockers, if used in pharmaceutical (as opposed to cosmetic) versions of my invention, do not need to undergo as lengthy and expensive a process to verify their safety and efficacy as used in pharmaceutical products. Examples include flutamide, cyproterone acetate, spironolactone, progesterone, or analogs or derivatives of any of these (e.g., 17-hydroxy-16-methylene-$\Delta^6$-progesterone, 17α-hydroxyprogesterone).

I have found several surprising things about testosterone blockers. First, they are not actually necessary for my invention to work; minoxidil alone is effective on 8% of patients, while the same amount of minoxidil administered with the proper amount of a penetration enhancer is effective on 35% of patients. Second, testosterone blockers added to such a mix are synergistically beneficial, increasing the efficacy from 35% to 85% of patients.

One testosterone blockler is the anti alopecia compound cioteronel. Cioteronel is the common name for hexahydro-4-(5-methoxyheptyl)-2(1H)-pentalenone. It is also known, or is commercially available, as X-ANDRON™, CPC-10997, CYOCTOLT™, and EXANDRON™. It is a clear, colorless oil, soluble in lipid and relatively non-polar solvents. Its preparation is disclosed in Kasha, W. J., *PCT Int'l Patent Application* 83/04,019 (1983), 101 *Chem. Abstr.* 23037k (1984). Its use is disclosed in U.S. Pat. No. 4,689, 345. Its inhibition of DHT binding in vitro is disclosed in *Rec. Adv. Chemotherapy* (Proc. $14^{th}$ Int'l Congr. Chemotherapy Antimicrob., Sect. 1) at 261–70 and 273–74 (Univ. Tokyo Press, 1985). Its cutaneous metabolism and clinical pharmacokinetics is disclosed in de Zeeuw et al., 7 *Pharm. Res.* 638 (1990), Weichers et al., 65 *Int. J. Pharm.* 77 (1990).

Another testosterone blocker is progesterone, pregn-4-ene-3, 20-dione (commercially available as CORLUTINA™, CORLUVITE™, CYCLOGETS™, GESTIRON™, GESTONE™, LIPOLUTIN™, LUTOCYCLIN™, PROGESTIN™, CP progesterone powder, etc . . . ). Progesterone is insoluble in water and soluble in alcohol, acetone, dioxane, and concentrated sulfuric acid. It is sparingly soluble in vegetable oils. Its isolation, structure and biological activity is described at length in Bardin et al. (eds.), Progesterone and Progestins (Raven Press, New York 1982). I prefer to use progesterone as the sole testosterone blocker.

Carrier Vehicles

The penetration enhancer and the vascular toner or testosterone blocker, or both, may be mixed with a carrier vehicle. You can use a variety of vehicles to make my invention. The vehicle is simply a cosmetically safe, medically safe solvent for the active ingredients. The vehicle should not adversely and significantly chemically react with the active ingredients.

For example, propylene glycol, water and isopropyl alcohol may be used as vehicles. These may be used alone or in combination.

The vehicle can optionally provide functions in addition to simply dissolving the active ingredients. For example, one can use a moisturizing vehicle, or a vehicle containing sunscreen. For a moisturizing or moisture retaining vehicle, one can use a vehicle made from a combination of (ranked in order of quantity used) water, mineral oil, petrolatum, lanolin, sorbitol solution, stearic acid, lanolin alcohol, cetyl alcohol, glyceryl stearate/PEG-100 stearate, triethanolamine, dimethicone, propylene glycol, tri(PPG-3 myristyl ether) citrate, disodium EDTA, methylparaben, ethylparaben, propylparaben, fragrance, xanthan gum, butylparaben, and methyldibromo glutaronitrile.

It may be desirable to use a vehicle containing one or more sunscreens. This is because my preparations are used on the tops of balding scalps. Balding scalps are often largely unprotected from sun damage, as the user may not wear headgear and the balding scalp lacks the sun shielding dense hair layer present on a healthy scalp. Adding sunscreen thus can protect the scalp from possible sun damage. Sunscreens, and vehicles containing sunscreen compounds, are widely known in the art. See, e.g., U.S. Pat. No. 4,522,807.

Other cosmetic vehicles are widely known in the art. I prefer to use VEHICLE/NT™ as the vehicle. I prefer to use VEHICLE/N(™) because it has a cosmetically attractive "feel" to the user. Vehicle/N(™) is commercially available from the Neutrogena Dermatologics division of Johnson & Johnson, Inc., New Brunswick, N.J. It is currently available in two formulations, regular and mild. They are both versatile liquid vehicles for extemporaneous compounding of topical drugs. Both formulations solublize selected dermatological agents and provide astringent and drying actions.

The VEHICLE/N(™) ingredients are SD alcohol 40 (45%), purified water (<45%), laureth-4 (>4%), isopropyl alcohol (4%) and propylene glycol (<4%). The VEHICLE/N(™) mild ingredients are purified water (>37.5%), SD alcohol-40 (37.5%), isopropyl alcohol (5%) and laureth-4 (<5%). To compound with VEHICLE/N, add the appropriate quantity of active ingredient to yield the intended concentration.

VEHICLE/N(™) is available as 50 mL of vehicle in a plastic bottle with applicator top. The bottle is filled only to ¾ capacity, to ensure proper mixing. For 50 mL of VEHICLE/N, use the following amounts:

| Desired Concentration | 0.1% | 0.2% | 0.5% | 1.0% |
|---|---|---|---|---|
| Bulk Active Tablets | 50 mg | 100 mg | 250 mg<br>1 × 250 mg | 500 mg<br>4 × 150 mg<br>1.2% soln |
| Desired Concentration | 2.0% | 3.0% | 4.0% | 5.0% |
| Bulk Active | 1.0 gm | 1.5 gm | 2.0 gm | 2.5 gm |

For fastest dissolution, when tablets are used, crush them to a powder and then add the powder to the vehicle. When capsules are used, add the capsule contents only to the vehicle, and discard the capsule shell. Shake the mixture gently. Most capsule contents and bulk active ingredients will dissolve within minutes, though some may take longer.

VEHICLE/N™ is available in a bottle with an APPLIDERM(™) applicator top. The APPLIDERM(™) applicator unit automatically filters the compounded mixture and provides a convenient, spill-proof, self-contained unit for topical application. To use the APPLIDERM(™) applicator unit, push the applicator firmly into the bottle using the white cap as a holder. Screw the cap all the way down to seat the applicator. Shake well. If tablets are dissolved in the vehicle, then the user should be instructed to allow the solution to stand overnight and to shake vigorously before the first use. VEHICLE/N(™) should not be used near fire or open flame due to alcohol content. Both VEHICLE/N(™) and VEHICLE/N(™) mild contain substantial alcohol and are not suitable for use in acute dermatoses. Stinging may be noted if used on irritated or abraded skin. Avoid contact with eyes or eyelids. If the product accidentally comes in contact with eyes, rinse thoroughly with water and contact physician. Keep out of reach of children. VEHICLE/N(™) and VEHICLE/N(™) mild are contraindicated in persons who have shown hypersensitivity to any of the listed ingredients.

Preferred Formulations

Given a constant amount of testosterone blocker or vascular toner, I have found that lower concentrations of penetration enhancer can decrease the efficacy of the final formulation, while higher concentrations of penetration enhancer increase the risk of adverse side effects due to systemic penetration of the other active ingredient(s).

Similarly, you may use different testosterone blockers for the same effect, and may use more or less of it. Using more testosterone blocker allows one to use relatively less penetration enhancer, or a weaker enhancer. Titration of the two components against one another is a conventional technique well known in the art of pharmaceutical and cosmetics formulation. Such techniques are already used to titrate formulations for the wide variety of trans-dermal drugs and cosmetics currently available.

For example, in a four ounce quantity of liquid containing 5 drops of trimethyl acetate, I prefer to use one percent (by volume) of soluble progesterone (U.S.P.).

A preferred formulation is:

| | |
|---|---|
| Minoxidil | 1.0 gm bulk powder |
| Soluble progesterone (U.S.P.) | 0.5 gm |
| Trimethyl acetate | 5 drops |
| Vehicle N (TM) | 50 mL |

The following preparation is acceptable, and within the scope of the claims, but I do not prefer it:

| | |
|---|---|
| Minoxidil | 1.0 gm bulk powder |
| Soluble progesterone (U.S.P.) | 0.5 gm |
| Methyl acetate | 5 drops |
| Vehicle N (TM) | 50 mL |

Alternatively, an ethyl alcohol—water—propylene glycol solution may be used as the diluents and vehicle. For 100 mL of this formulation, use:

| | |
|---|---|
| ethyl alcohol 95% | 75.5 cc |
| purified water | 18.5 cc |
| propylene glycol | 6.0 cc |
| progesterone | 1.5 gm |
| minoxidil | 2.0–5.0 gm |
| methyl acetate | 5.0 gtts |

These are my preferred formulations. These may be varied as desired, but it is necessary to watch for unwanted side effects possibly due to unwanted systemic penetration of the active ingredient(s). For example, minoxidil is pharmaceutically and cosmetically effective topically at anywhere from about 0.01 grams to about 50 grams per four ounces, depending on the frequency of topical administration. Testosterone blockers are also pharmaceutically and cosmetically effective topically at anywhere from about 0.01 grams to about 50 grams per four ounces, depending on the frequency of topical administration. With the higher concentrations, however, increasing the amount of penetration enhancer creates a greater risk of adverse side effects.

Summary

I have discussed several different specific formulas. I have found these most useful. One can, however, vary the constituents to achieve the same effect without having a substantially different product. For example, one can use a different testosterone blocker, or a weaker penetration enhancer in a higher concentration.

Thus, the legal scope of my patent is not limited to the specific examples I discuss herein; rather, the legal coverage of this patent is defined by the appended claims and their equivalents.

What is claimed is:

1. A topical composition of matter comprising:
   a) a 5α-reductase inhibitor,
   b) minoxidil, and
   c) trimethyl acetate.
2. The composition of claim 1, wherein said trimethyl acetate is present in a concentration sufficient to aid in penetrating skin to a depth of approximately the depth of hair bulbs.
3. The composition of claim 1, wherein said 5α-reductase inhibitor comprises progesterone.
4. The composition of claim 3, wherein the ratio of 5α-reductase inhibitor to minoxidil in the composition is approximately 0.5 grams: 1 gram.
5. An article of manufacture comprising:
   a) the composition of claim 3, and
   b) a label indicating cosmetic use.
6. An article of manufacture comprising:
   a) the composition of claim 3, and
   b) a label indicating pharmaceutical use.
7. The article of manufacture of claim 6, wherein said pharmaceutical use comprises alopecia.
8. The composition of claim 3, further comprising a sunscreen.
9. A method comprising topically administering a composition of matter comprising:
   a) a 5α-reductase inhibitor,
   b) minoxidil, and
   c) trimethyl acetate.
10. The method of claim 9, wherein said trimethyl acetate is present in a concentration sufficient to aid in penetrating skin to a depth of approximately the depth of hair bulbs.
11. The method of claim 9, wherein said 5α-reductase inhibitor comprises progesterone.
12. The method of claim 11, wherein the ratio of 5α-reductase inhibitor to minoxidil in the composition is approximately 0.5 grams: 1 gram.
13. The method of claim 9, used for a cosmetic use.
14. The method of claim 9, used for a pharmaceutical use.
15. The method of claim 14, wherein said pharmaceutical use is preventing or treating alopecia.
16. The method of claim 11, further comprising administering a sunscreen.
17. A method for improving the skin penetration of a topically-applied compound, the method comprising topically administering said compound together with trimethyl acetate.

* * * * *